United States Patent [19]
Boar et al.

[11] Patent Number: 5,385,921
[45] Date of Patent: Jan. 31, 1995

[54] PHARMACEUTICAL FORMULATIONS

[75] Inventors: Bernard R. Boar, Letchworth; Alan J. Cross, West Byfleet; Alfred R. Green, Southmoor, all of Great Britain; Curt-Eric Hagberg, Upplands Väsby, Sweden

[73] Assignee: Aktiebolaget Astra, Sodertalje, Sweden

[21] Appl. No.: 744,914

[22] Filed: Aug. 14, 1991

[30] Foreign Application Priority Data

Aug. 15, 1990 [SE] Sweden .................. 9002659

[51] Int. Cl.$^6$ .................. A01K 31/425
[52] U.S. Cl. .................. 514/365
[58] Field of Search .................. 548/203; 514/365

[56] References Cited

U.S. PATENT DOCUMENTS 4,212,709  7/1980  Patsch et al. .................. 548/203

FOREIGN PATENT DOCUMENTS 0230370  1/1987  European Pat. Off. .
196140   5/1965  Sweden .

OTHER PUBLICATIONS

M. Ende, et al., Urinary Metabolites of Clomethiazole, *Arzneim-Forsch/Drug. Res. 29(II)* Nr. 11, pp. 1655–1658 (1979).
R. Pal, et al., Thiomethylation and Thiohydroxylation–A New Pathway of Metabolism of Heterocyclic Compounds, *Xenobiotica*, vol. 12, No. 12, pp. 813–820 (1982).
C. P. Offen, et al., 4,5-Dimethylthiazole-N-Oxide-S-Oxide; A Metabolite of Chlormethiazole In Man, *Xenobiotica*, vol. 15, No. 6, pp. 503–511 (1985).
A. R. Green, et al., A simple Intravenous Infusion Method In Rodents for Determining the Potency of Anticonvulsants Acting Through GABAergic Mechanisma, *J. Pharm. Pharmacol.* 41; 879–800 (1989).
Goodman and Gilman's *The Pharmacological Basis of Therapeutics* Seventh Edition, pp. 13, 357, 454 and 455 (1985).
D. V. Parke, *Recent Advances in Pharmacology*, 4th Ed., p. 68, (1968) reprinted In Taylor et al. *Introductory Medicinal Chemistry*, p. 182.
Alfred Burger, *A Guide To The Chemical Basis of Drug Design*, p. 137 (1983).
Louis Low et al., Prolonged Intravenous Use of Chlormethiazole (Heminevrin), *British Medical Journal*, p. 484 (1980).
F. Nouailhat et al., abstract of Treatment of Status Epilepticus In The Adult, *Rev. Electroencephalogr. Neurophysiol Clin.* 14, 237 (1985).
C. Carlsson et al., Influence of Chlormethiazole On Cerebral Blood Flow and Oxygen Consumption In The Rat, and Its Effect on the Recovery Of Cortical Energy Metabolism After Pronounced, Incomplete Ischaemia, *Acta. Anaesth. Scand.* 23, 259–266 (1979).
I. Piehlmayr et al., Studies On Blood Flow, Metabolism and Autoreglation Of The Brain Under Chlormethiazol(Distraneurin ®)) In Animal Experiments, *Annesthesist.* 22, 496–500 (1973).
M. G. Mead et al., Confusion And Hypnotics In Demented Patients, *Journal Of The Royal College Of General Practitioners* 32, 763–765 (1982).
Paul L. Ornstein, et al., Synthesis and Pharmacology of A Series of 3- and 4-(Phosphonoalkyl)Pyridine-and (List continued on next page.)

*Primary Examiner*—Robert Gerstl
*Attorney, Agent, or Firm*—White & Case

[57] ABSTRACT

New pharmaceutical formulations comprising 5-(2-chloro-1-hydroxyethyl)-4-methylthiazole or optical isomers or a pharmaceutically acceptable salt or solvate thereof.

7 Claims, No Drawings

OTHER PUBLICATIONS

-Piperiding-2-Carboxylic Acids. Potent N-Methyl-D-Aspartate Receptor Antagonists, *J. Med. Chem.* 32, 827 (1989).

C. W. Cotman et al., Excitatory Amino Acids In The Brain-Focus On NMDA Receptors, *TINS*, vol. 10, No. 7, pp. 263–265 (1987).

William F. Maragos, et al., Glutamate dysfunction in Alzheimer's disease: an hypothesis, *TINS 10*, 65–68 (1987).

N. T. Gurusinghe, et al., Chlormethiazole In The Management Of Post-Cranitomy Seizures, *Acta. Psychiatr. Scand. Suppl.* 329, vol. 73, pp. 189–193 (1986).

S. A. Ather, et al., A Comparison of Chlormethiazole and Thioridazine In Agitated Confusional States of the Elderly, *Acta. Phychiatr. Scand. Suppl.* 329, vol. 73, pp. 81–91 (1986).

T. V. Stanley, Oral Chlormethiazole in Childhood Epilepsy, *Archives of Disease in Childhood*, vol. 57, pp. 242-3 (1982).

PHARMACEUTICAL FORMULATIONS

DESCRIPTION

1. Field of the Invention

The present invention relates to 5-(2-chloro-1-hydroxyethyl)-4-methylthiazole for use in therapy and pharmaceutical formulations comprising said compound. The invention also relates to the use of said compound for the manufacture of a medicament. In a further aspect the invention relates to a method for prevention or treatment of neurodegeneration or for obtaining sedation or anticonvulsant effect by administering such a compound in a sufficient amount. Another aspect of the invention is a pharmaceutical formulation for use in the prevention or treatment of neurodegeneration or for obtaining sedation or anticonvulsant effect comprising said compound as active ingredient.

2. Background of the Invention

There are various publications on the metabolism of chlormethiazole. The metabolites of special interest in connection with the present invention are 5-(2-chloro-1-hydroxyethyl)-4-methylthiazole having the formula

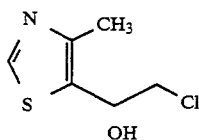

and optical isomers, or a pharmaceutically acceptable salt or solvate thereof. Said compound is reported in the literature as a metabolite identified primarily by mass spectrometry. For the sake of simplicity said compounds are hereinafter referred to as 5-(2-chloro-1-hydroxyethyl)-4-methylthiazole.

In Arzneim.-Forsch./Drug Res. 29 (II), Nr 11 (1979), pp. 1655–1658, it is reported by Ende. M., Spiteller, G., Remberg G., and Heipertz, R. that one of the metabolites of chlormethiazole in human urine seems to be 5-(2-chloro-1-hydroxyethyl)-4-methylthiazole (substance 9 on page 1658).

5-(2-chloro-1-hydroxyethyl)-4-methylthiazole is used by Pal, R. and Spiteller, G. in Xenobiotica, 1982, vol. 12, No. 12, pp. 813–820, for comparision of chlormethiazole metabolites using mass spectrometry.

Offen, C. P., Frearson, M. J., Wilson, K. and Burnett, D. disclose in Xenobiotica, 1985, vol. 15, No. 6, pp. 503–511 six major metabolite peaks of chlormethiazole in urine. Peak 4 was identified as 5-(2-chloro-1-hydroxyethyl)-4-methylthiazole.

The published data in the above-mentioned documents refers mainly to structural identification rather than the pharmacological properties of the metabolites. Thus, the prior art does not disclose any pharmacological properties of 5-(2-chloro-1-hydroxyethyl)-4-methylthiazole.

DISCLOSURE OF THE INVENTION

The present invention refers to a certain chlormethiazole metabolite namely 5-(2-chloro-1-hydroxyethyl)-4-methylthiazole, optical isomers or a pharmaceutically acceptable salt or a solvate thereof. Within the scope of the present invention are the two optical isomers (+ and −) as well as the racemic form (±).

Different aspects of the present invention are:

- a pharmaceutical formulation comprising 5-(2-chloro-1-hydroxyethyl)-4-methylthiazole or optical isomers, a pharmaceutically acceptable salt or solvate thereof as active ingredient;
- 5-(2-chloro-1-hydroxyethyl)-4-methylthiazole and optical isomers or a pharmaceutically acceptable salt or a solvate thereof for use in therapy, especially as an agent for prevention or treatment of neurodegeneration or as an anticonvulsive or sedative agent;
- the use of 5-(2-chloro-1-hydroxyethyl)-4-methylthiazole, and optical isomers or a pharmaceutically acceptable salt or solvate thereof, for the manufacture of a medicament for the prevention or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease; or for the manufacture of a medicament having anticonvulsant or sedative effect;
- a method for the prevention or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease, or for obtaining sedation or anticonvulsant effect in a host in need of such treatment by administering a sufficient amount of 5-(2-chloro-1-hydroxyethyl)-4-methylthiazole or optical isomers or a pharmaceutically acceptable salt or solvate thereof;
- a pharmaceutical formulation for use in the prevention or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease, or for use in obtaining sedation or anticonvulsant effect in a host in need of such treatment comprising 5-(2-chloro-1-hydroxyethyl)-4-methylthiazole or optical isomers or a pharmaceutically acceptable salt or a solvate thereof as active ingredient.

The pharmaceutically acceptable salts are new and include the hydrochloride salt, salt with ethandisulphonic acid, salts with methane polysulphonic acids, ethane monosulphonic acids and ethane polysulphonic acids. The salt with ethanedisulphonic acid and the hydrochloride salt are the preferred salts.

The racemate of 5-(2-chloro-1-hydroxyethyl)-4-methylthiazole can be resolved by using standard techniques, e.g. HPLC or crystallisation of salts.

The clinically most important fields of use are considered to be the prevention and/or treatment of neurodegeneration in connection with stroke, cerebral ischaemia, multi-infarct dementia and hypoxia, and obtaining sedation or anticonvulsant effect in a host in need of such treatment.

The effectiveness of 5-(2-chloro-1-hydroxyethyl)-4-methylthiazole for use according to the present invention in the prevention or treatment of neurodegeneration may be demonstrated by the ability to decrease damage to the CA1/CA2 hippocampal pyramidal neurones in gerbils following ischaemia induced by a period of occlusion of the carotid arteries followed by reperfusion. The detailed mechanisms that underlie ischaemia-induced degeneration of hippocampal neurones have yet to be clarified, but the above mentioned gerbil test system has been widely used as a predictive model of neuroprotective activity (see, for example, B. J. Alps, C. Calder, W. K. Hass and A. D. Wilson, Brit. J. Pharmacol., 1988, 93, 877–883; R. Gill, A. C. Foster and G. N. Woodruff, J. Neuroscience, 1987, 7, 3343–3349.

It is a particular feature that the compound of the present invention is effective in preventing and/or treating neurodegeneration even when administered solely following the ischaemic insult, even several hours after the ischaemic insult. It is to be expected that the efficacy when administered after induction of ischaemia is of particular relevance to the likely clinical utility.

The effectiveness of 5-(2-chloro-1-hydroxyethyl)-4-methylthiazole for use according to the present invention in obtaining sedation may be demonstrated by the ability of the compound to suppress locomotor activity as described below (S. O. Ögren, Acta psychiatr. scand. Suppl. 329, Vol. 73, 1986, pages 13–29.)

The effectiveness of 5-(2-chloro-1-hydroxyethyl)-4-methylthiazole for use according to the present invention in obtaining an anticonvulsant effect is demonstrated as further described below.

The administration in the novel method of treatment of this invention may conveniently be oral, rectal, or parenteral at a dosage level of, for example, about 1 to 3000 mg/kg, preferably about 10 to 1000 mg/kg and especially about 25 to 250 mg/kg and may be administered on a regimen of 1 to 4 hours per day. The dose will depend on the route of administration, a particularly preferred route being by intravenous infusion of an aqueous solution containing 5-(2-chloro-1-hydroxymethyl)-4-methylthiazole ethanedisulphonate, for example, an aqueous solution containing 5-(2-chloro-1-hydroxymethyl)-4-methylthiazole ethanedisulphonate 8 mg/ml. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, syrups, powders or granules for oral administration; sterile parenteral solutions or suspensions for parenteral administration; or as suppositories for rectal administration.

To produce pharmaceutical formulations containing a compound according to the present invention in the form of dosage units for oral application, e.g. lactose, saccharose, sorbitol, mannitol, starches such as potato starch, corn starch or amylopectin, cellulose derivatives, a binder such as gelatine or polyvinylpyrrolidone, and a lubricant such as magnesium stearate, calcium stearate, polyethylene glycol, waxes, paraffin, and the like, and then compressed into tablets. If coated tablets are required, the cores, prepared as described above, may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compounds.

For the preparation of soft gelatine capsules, the active substance may be admixed with e.g. a vegetable oil or polyethylene glycol. Hard gelatine capsules may contain granules of the active substance using either the above-mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Dosage units for rectal application can be solutions or suspensions or can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from about 0.5% to about 10% by weight. These solutions may also contain stabilizing agents and/or buffering agents and may conveniently be provided in various dosage unit ampoules.

Methods of preparation of
5-(2-chloro-1-hydroxyethyl)-4-methylthiazole and salts thereof 5-(2-Chloro-1-hydroxyethyl)-4-methylthiazole ethandisulphonate To a suspension of 4-methyl-5-vinylthiazole (8.76 g, 70 mmol) in 80 ml water and 8 ml acetic acid is added tert.-butyl hypochlorite (7.8 g, 72 mmol) in 45 min at ambient temperature. After stirring for 1 hour at room temperature 100 ml diethyl ether is added and the phases separated. The solvent is removed from the organic phase and the residue purified by flash chromatography to yield 1.85 g of an oil.

This oil is dissolved in 3.5 ml isopropanol, 3 ml water and concentrated sulphuric acid (0.5 g). After addition of calcium ethandisulphonate (1.15 g), the mixture is stirred at 40° for 3 hours. The precipitate is filtered off and the filtrate is evaporated with 3 successive additions of isopropanol. The residue is recrystallized from a solution of 20 ml diisopropyl ether, 30 ml ethanol and 15 ml methanol to yield 1.35 g of a white crystalline product. M.p. 165°–168° C.

$^1$H NMR spectrum of the ethanedisulphonate (in DMSO) is 2.5 (3H,s), 2.85 (2H,s), 3.85 (2H,d), 4.8 (broad) 5.25 (IH,t) 9.25 (IH,s) ppm.

5-(2-chloro-1-hydroxyethyl)-4-methylthiazole hydrochloride salt 5-(2-chloro-1-hydroxyethyl)-4-methylthiazole free base was treated with a solution of hydrogen chloride in ethanol. Diethyl ether was added and the resultant precipitate was collected and recrystallized from a methanol-diethyl ether mixture to give the hydrochloride salt, m.p. 136°–136.5° C.

The $^1$H NMR spectrum (in DMSO) is 2.5 (3H,s), 3.85 (2H,d), 5,25 (IH,t), 8.4 (2H, broad) and 9.45 (IH,s) ppm.
$^{13}$C NMR spectrum (in DMSO) 13.9, 49.4, 65.8, 135.9, 145.0 and 153.5 ppm.

Methods of optical resolution of 5-(2-chloro-1-hydroxyethyl)-4-methylthiazole (a) 5-(2-chloro-1-hydroxyethyl)-4-methylthiazole (2 g) in dry dichloromethane (200 ml) was treated with triethylamine (10 ml) followed by (1S)-(−)-camphanic chloride (9.7 g). The mixture was stirred at room temperature for two hours. The reaction mixture was washed with 1N sodium hydroxide solution followed by water. The organic layer was separated, dried and evaporated under reduced pressure to yield an oil. This oil was purified by flash chromatography on silica gel to yield the (1S)-(−)camphanate ester of 5-(2-chloro-1-hydroxyethyl)-4-methylthiazole (diastereomeric mixture) as an oil which readily solidified. The $^1$H NMR spectrum of this material in CDCl$_3$ showed, in part, peaks at 0.89 and 0.94 (combined integral 3H), 1.04 and 1.06 (combined integral 3H) and 1.10 (3H, broad s) ppm.

(b) The diastereomeric mixture of esters obtained as in (a) above was separated into the individual diastereoisomers by HPLC using polygosil silica, 7 μm, 2×25 cm column, eluent 70% hexane: 30% ethyl acetate; flow rate 20 ml/minute; UV detector.

Diastereomer 1: m.p. 127°–128° C. $^1$H NMR (CDCl$_3$) 0.94, 1.04 and 1.10 (each 3H, s) ppm.

Diastereomer 2: m.p. 120°–121° C. $^1$H NMR (CDCl$_3$) 0.89, 1.06 and 1.10 (each 3H, s) ppm.

(c) The diastereomeric mixture of esters obtained as in (a) above (5 g) in acetone (100 ml) was treated with a solution of (1S)-(+)-10-camphorsulphonic acid (1.3 g) in acetone (100 ml). The mixture was stirred at room temperature whereupon a white solid crystallised out. This solid was collected by filtration, washed and dried to give material m.p. 178°–179° C. which was shown by NMR spectroscopy to be optically pure [0.88, 1.0, 1.07, 1.08 and 1.14 (each 3H, s) ppm]. This salt was reconverted into the free base to give (1S)-(−)-camphanate ester of 5-(2-chloro-1-hydroxyethyl)-4-methylthiazole diastereoisomer 1 ($^1$H NMR 0.94, 1.04 and 1.1 (each 3H, s) ppm). HPLC showed this material to be optically pure and to be identical to diastereoisomer 1 obtained in (b) above by preparative HPLC separation.

(d) The diastereomeric mixture of esters obtained as in (a) above (200 mg) in a minimum volume of acetone was treated with (1S)-(−)-camphanic acid (117 mg) also in the minimum volume of acetone. The resulting solution was left overnight at −20° C. The white solid that separated was collected, washed and dried to give material which was shown by NMR spectroscopy to be optically pure [0.90, 1.02, 1.08, 1.105, 1.115 and 1.14 (each 3H, s) ppm]. This salt was reconverted into the free base to give (1S)-(−)-camphanate ester of 5-(2-chloro-1-hydroxyethyl)-4-methylthiazole diastereoisomer 2 ($^1$H NMR 0.89, 1.06 and 1.10 (each 3H, s) ppm). HPLC showed this material to be optically pure and to be identical to diastereoisomer 2 obtained in (b) above by preparative HPLC separation.

(e) The (1S)-(−)-camphanate ester of 5-(2-chloro-1-hydroxyethyl)-4-methylthiazole diastereoisomer 1 (obtained as in (b) or (c) above) or diastereoisomer 2 (obtained as in (b) or (d) above) were separately hydrolysed using an excess of 5M hydrochloric acid in methanol at 60° C. to give the (+)- and (−)-isomers of 5-(2-chloro-1-hydroxyethyl)-4-methylthiazole as oils.

$^1$H NMR (CDCl$_3$) 2.5 (3H, s), 3.7 (2H), 5.1 (1H) and 8.7 (1H) ppm.

Analytical HPLC on a chiral AGP column using phosphate buffer pH 7.3 indicated that each isomer was, within the limits of detection, optically pure.

Pharmacological tests

Animals used were male Wistar rats (140–170 g) and male TO mice (18–30 g).

All drugs were dissolved in isotonic saline. Weights refer to the free base.

Neuroprotection studies

Ischaemia was induced in gerbils, by occlusion of the carotid arteries following the accepted general procedure as described in, for example, EP 230 370 and R. Gill, A. C. Foster and G. N. Woodruff, J. Neuroscience, 1987, 7, 3343–3349.

Typical procedures and results are exemplified as follows:

Administration of the Test Compound Following Induction of Ischaemia.

Ischaemia was induced in the animals by 5 minute occlusion of both carotid arteries. Body temperature was maintained at 37° C. throughout. Restoration of blood flow after occlusion was checked visually and the animals were allowed to survive for 4 days. The extent of neuronal degeneration in the hippocampus was then assessed. The test compounds were adminstered (i.p.) as a single dose 60 minutes following occlusion. No administration was made prior to the occlusion. Typical results are shown in Table 1. As is seen in Table 1,5-(2-chloro-1-hydroxyethyl)-4-methylthiazole hydrochloride salt was effective in reducing the damage to the CA1/CA2 hippocampal neurones.

TABLE 1

| Test Compound | Dose | Time of Dosing after Induction of Ischaemia | Number of Animals | % Damage to CA1/CA2 Hippocampal Neurones | |
|---|---|---|---|---|---|
| None | — | — | 12 | 92 | ±7 |
| 5-(2-chloro-1-hydroxyethyl-4-methylthiazole hydrochloride salt | 100 mg/kg | 60 minutes | 8 | 64 | ±8 |

Sedation Studies

The test drug was administered to mice and starting 20 min later locomotor activity was recorded for a 30 min period. Activity was monitored using an infra-red light beam interruption system in cages measuring 40 cm × 40 cm. Data are expressed as the dose required to reduce locomotor activity by 50% (ED$_{50}$). A typical result is shown in Table 2.

Anticonvulsant Studies

Pentylenetetrazol (PTZ) seizures

Seizure threshold was assessed in rats by measurement of the dose of PTZ required to elicit a seizure when infused through a tail vein. PTZ (10 mg/ml) was infused into the tail vein at a rate of 2.6 ml/min and the time to the first clonic convulsion measured. Seizure threshold was calculated as described by Green & Murray, J. Pharm. Pharmacol. 1989, 41: 879–880. Drugs were administered 15 min before the PTZ. Data are expressed as the dose required to increase seizure threshold by 50% ($TI_{50}$).

N-methyl-D-aspartate (NMDA) Seizures

Groups of eight mice were injected with NMDA (300 mg/kg i.p.) and the number of mice demonstrating tonic convulsions within the following 15 min period were recorded. Drugs were adminstered 15 min before the NMDA, and data are expressed as the dose required to decrease the incidence of tonic convulsions by 50% ($ED_{50}$).

Typical seizure results are shown in Table 2.

TABLE 2

|  | 5-(2-chloro-1-hydroxyethyl)-4-methylthiazole ethanedisulphonate salt |
| --- | --- |
| Sedation ($ED_{50}$ mg/kg) | 52 |
| PTZ seizures ($TI_{50}$ mg/kg) | 34 |
| NMDA seizures ($ED_{50}$ mg/kg) | 40 |

CONCLUSIONS

As demonstrated by the above results, the effectiveness of 5-(2-chloro-1-hydroxyethyl)-4-methylthiazole in decreasing damage to the CA1/CA2 hippocampal neurones in gerbils following ischaemic insult clearly illustrates the usefulness of this compound in preventing neurodegeneration. The compound is therefore considered to be useful for the prevention and/or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease.

As demonstrated by the above results, the ability of 5-(2-chloro-1-hydroxyethyl)-4-methylthiazole to reduce locomotor activity establishes sedative/hypnotic properties indicative of likely clinical utility as a sedative.

As demonstrated by the above results, the ability of 5-(2-chloro-1-hydroxyethyl)-4-methylthiazole to prevent seizures establishes anticonvulsant properties indicative of usefulness in the clinic for the treatment of different types of convulsive states, such as, for example, status epilepticus, pre-eclampsia and delirium tremens.

What we claim is:

1. A method for the treatment of neurodegeneration involving loss of neuronal structure following a pathological insult in the brain of a human subject comprising administering to said subject a therapeutically effective amount of 5-(2-chloro-1-hydroxyethyl)-4-methylthiazole, an optical isomer thereof or a pharmaceutically acceptable salt or solvate thereof.

2. The method of claim 1 wherein the pathological insult is caused by stroke.

3. The method of claim 1 wherein the pathological insult is caused by cerebral ischaemia.

4. The method of claim 1 wherein the pathological insult is caused by hypoxia.

5. The method of claim 1 wherein the pathological insult is caused by multi-infarct dementia.

6. A method for the treatment of neurodegeneration involving loss of neuronal structure following a pathological insult in the brain of a human subject caused by stroke, cerebral ischemia, hypoxia or multi-infarct dementia, comprising administering to said subject a therapeutically effective amount of 5-(2-chloro-1-hydroxyethyl)-4-methylthiazole, an optical isomer thereof or a pharmaceutically acceptable salt or solvate thereof, in the dosage range of about 10–1000 mg/kg body weight, in combination with a pharmaceutically acceptable carrier.

7. The method of claim 6 wherein the dosage range is 25–250 mg/kg body weight.

* * * * *